(12) United States Patent  
Blette

(10) Patent No.: US 8,545,613 B2
(45) Date of Patent: Oct. 1, 2013

(54) TATTOO TRANSFER PATTERN PRINTED BY AN INK JET PRINTER

(75) Inventor: Russell E. Blette, Hastings, MN (US)

(73) Assignee: RandD Enterprises of San Jose, LLC, Hastings, MN (US)

( * ) Notice: Subject to any disclaimer, the term of this patent is extended or adjusted under 35 U.S.C. 154(b) by 222 days.

(21) Appl. No.: 13/096,535

(22) Filed: Apr. 28, 2011

(65) Prior Publication Data

US 2011/0268873 A1 Nov. 3, 2011

Related U.S. Application Data

(60) Provisional application No. 61/329,358, filed on Apr. 29, 2011.

(51) Int. Cl.
*C09D 11/00* (2006.01)
*A61L 2/08* (2006.01)
*A61L 2/20* (2006.01)

(52) U.S. Cl.
USPC ............... 106/31.33; 106/31.03; 106/31.32; 106/31.58; 422/22

(58) Field of Classification Search
USPC .......... 106/31.03, 31.27, 31.32, 31.33, 31.58; 422/22; 424/401, 63
See application file for complete search history.

(56) References Cited

U.S. PATENT DOCUMENTS

| | | | | |
|---|---|---|---|---|
| 4,169,169 A | | 9/1979 | Kitabatake | |
| 4,842,646 A | * | 6/1989 | Gamblin | 106/31.36 |
| 5,015,263 A | * | 5/1991 | Albrecht et al. | 8/680 |
| 5,397,387 A | * | 3/1995 | Deng et al. | 106/31.37 |
| 5,601,859 A | * | 2/1997 | Penaluna | 426/5 |
| 5,676,401 A | * | 10/1997 | Witkowski et al. | 283/81 |
| 5,800,601 A | * | 9/1998 | Zou et al. | 106/31.65 |
| 5,817,385 A | * | 10/1998 | Stanislav | 428/40.2 |
| 6,013,122 A | * | 1/2000 | Klitzman et al. | 106/31.03 |
| 6,042,881 A | | 3/2000 | Ewan | |
| 6,074,721 A | * | 6/2000 | Moore et al. | 428/42.1 |
| 6,106,852 A | * | 8/2000 | Vineberg | 424/402 |
| 6,299,967 B1 | | 10/2001 | Collins et al. | |
| 6,341,831 B1 | * | 1/2002 | Weber et al. | 347/1 |
| 6,896,724 B2 | * | 5/2005 | Sun et al. | 106/31.86 |
| 7,431,956 B2 | * | 10/2008 | Baydo et al. | 426/250 |
| 7,431,957 B2 | * | 10/2008 | Baydo et al. | 426/250 |
| 7,435,439 B2 | * | 10/2008 | Morgan et al. | 426/383 |
| 2008/0193725 A1 | * | 8/2008 | De Saint-Romain | 428/195.1 |
| 2009/0325221 A1 | * | 12/2009 | Long et al. | 435/34 |

OTHER PUBLICATIONS

Webpage, www.tattojohnny.com, 2009.

* cited by examiner

*Primary Examiner* — Helene Klemanski
(74) *Attorney, Agent, or Firm* — DuFault Law Firm, P.C.; Dustin R. DuFault

(57) ABSTRACT

A composition of matter includes a cationic dye and a solvent, wherein the composition does not have particles that are greater than 25 microns in diameter. The disclosure also describes a method for producing a composition of matter. An ink jet cartridge includes the composition of matter. A device includes a substrate having an image printed thereon with the composition of matter. A method includes using an inkjet printer to print a graphic on a first major surface of a substrate; moistening a user's skin surface; contacting the first major surface of the substrate to the user's moistened skin surface; and removing the substrate from the user's skin surface, thereby leaving a mirror image of the printed graphic on the user's skin surface. Moreover, an art kit includes a first substrate having a graphic printed thereon and a second substrate having a mirror image of the graphic printed thereon.

9 Claims, 3 Drawing Sheets

TATTOO TRANSFER PATTERN PRINTED BY AN INK JET PRINTER

CROSS-REFERENCE TO RELATED APPLICATION

The present application is based on and claims the benefit of U.S. provisional patent application Ser. No. 61/329,358, filed Apr. 29, 2011, the content of which is hereby incorporated by reference in its entirety.

BACKGROUND

The tattooing process starts with the selection of artwork by the customer. Customers may choose from art on display that has already been drawn (commonly referred to as "flash" art) or may have the artist create a new work. The tattoo artist produces an outline of the artwork, which is then transferred to the skin using image transfer paper and then used as a reference for the transdermal ink application.

Two types of image transfer paper are generally used. Hectograph paper can be used with a pressure method to transfer an outline from a sheet of plain paper onto the transfer paper. Suitable pressure transfer methods include hand tracing or the use of a dot matrix printer. Thermal paper can be used for hand tracing or with a thermal copier to transfer an outline from a sheet of regular paper onto the transfer paper.

Both types of transfer paper, hectograph and thermal, are typically supplied in a 3-layer format consisting of a flexible top white transfer sheet, an intermediate protective sheet and a third sheet carrying a dye to be transferred to the bottom surface of the transfer sheet and ultimately onto skin. Thermal paper may also have a fourth, bottom sheet that holds the original artwork sheet in place when using a thermal copier. The dye on these multi-layer transfer papers is usually purple in color and is water-insoluble but easily removed with alcohol. For hand tracing, an artist obtains or produces a design outline on plain paper. After removing the intermediate protective sheet from the transfer paper, the artist places the plain paper on top of the white transfer sheet and traces the design outline using a pen or pen-like device with downward pressure on the layered sheets. A dot matrix printer can alternatively be used to imprint the design onto the transfer sheet. The pressure from either the pen or printer causes the dye from the bottom sheet to attach to the bottom side of the transfer sheet.

A thermal copier or printer produces images by heating thermal paper, as seen on older fax machines, cash registers, ATM receipt printers, and lottery ticket printers, for example. Using a thermal copier, a design on plain paper is copied with dye onto the transfer sheet of a layered thermal transfer paper. Using either transfer method, once the design has been attached to the transfer sheet, the design is cut from the transfer sheet, resulting in a "stencil" that is then applied to the customer's skin. First, the customer's skin is cleaned and shaved. The skin is moistened with a transfer lotion to facilitate dye adhesion on the skin. A glycerin-based solution containing sodium stearate (such as Speed-Stick™ deodorant, for example) is especially suitable. Then the stencil is pressed onto the skin, with the dye contacting the moistened skin. The transfer sheet is carefully removed, leaving the dye design on the skin.

Both methods of stencil creation require the production of a single stencil at a time on expensive specialty transfer papers. The hand tracing method is laborious, slow, and possibly inaccurate, depending on the skill of the artist. Sharpness of the outline is limited using a dot matrix printer method. The thermal copier method requires the use of expensive specialty equipment. The most commonly used papers only provide for a reference design consisting of a single color.

Moreover, because the resulting reference design lies on the skin surface, the dyes therein are pushed into the skin during the tattooing process. However, the papers and equipment traditionally used are not specially formulated for use on human skin and are typically not sterilized, thereby possibly leading to infection or other health concerns.

SUMMARY

In one aspect, a composition of matter comprises a cationic dye and a solvent, wherein the composition does not have particles that are greater than 25 microns in diameter. In another aspect, a method for producing a composition of matter comprises producing a mixture comprising a cationic dye and a solvent and filtering the mixture to obtain a composition that does not have particles that are greater than 25 microns in diameter. In yet another aspect, an ink jet cartridge comprises a first compartment having a first liquid therein, the first liquid comprising a first cationic dye and a solvent, wherein the first liquid does not have particles that are greater than 25 microns in diameter. In still another aspect, a device comprises a substrate having an image printed thereon comprising a first cationic dye and solvent formulation that does not have particles that are greater than 25 microns in diameter. In yet another aspect, a method comprises using an inkjet printer to print a graphic on a first major surface of a substrate; moistening a user's skin surface; contacting the first major surface of the substrate to the user's moistened skin surface; and removing the substrate from the user's skin surface, thereby leaving a minor image of the printed graphic on the user's skin surface. Moreover, an art kit comprises a first substrate having a graphic printed thereon; and a second substrate having a mirror image of the graphic printed thereon, wherein the mirror image on the second substrate can be transferred to a person's skin to yield a facsimile of the graphic on the person's skin.

BRIEF DESCRIPTION OF THE DRAWINGS

The disclosed subject matter will be further explained with reference to the attached figures, wherein like structure or system elements are referred to by like reference numerals throughout the several views.

DETAILED DESCRIPTION OF ILLUSTRATIVE EMBODIMENTS

Figure 1:
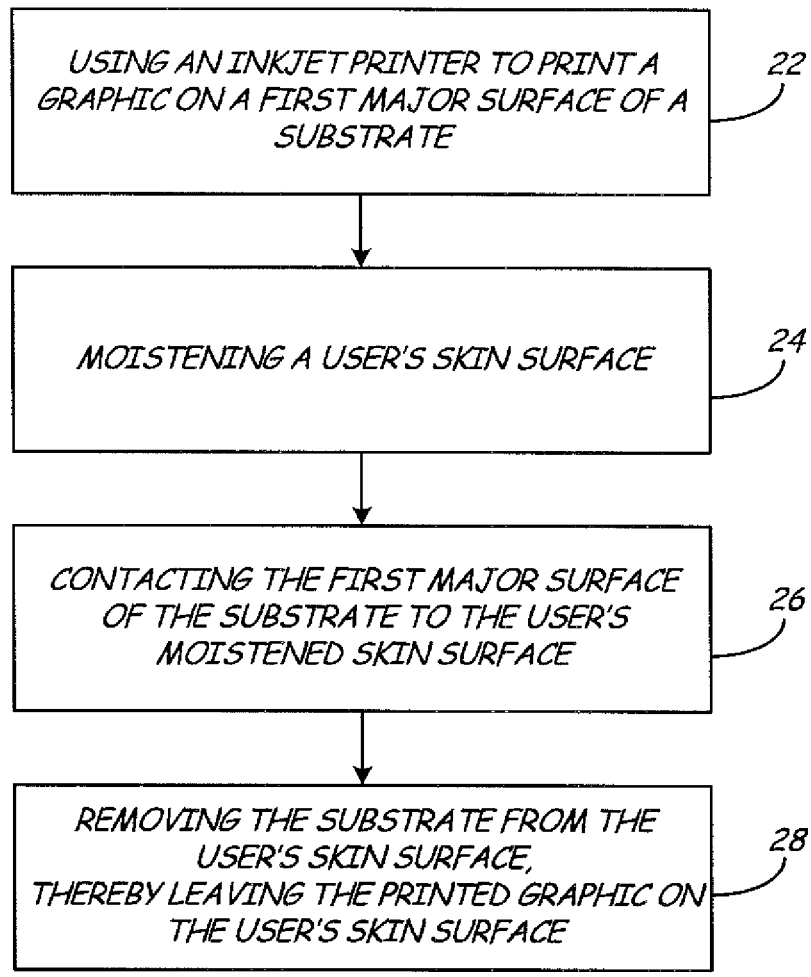
FIG. 1 is a block diagram describing an exemplary method of the present disclosure.

This disclosure relates to methods and articles of manufacture such as dyes that allow for the creation of tattoo stencils easily, quickly and accurately using a common and inexpensive ink jet printer. Moreover, the disclosed methods can be used with readily available, inexpensive papers. Additionally, a reference stencil comprising a plurality of colors, patterns and shading is possible with the disclosed methods and articles of manufacture. Further, the articles of manufacture may be sterilized for hygienic use on human skin.

After a tattoo design (typically an outline) is transferred to the skin, the artist uses the outline as a reference for the transdermal application of colored pigments using needles. Because tattooing creates wounds in the skin that bleed or ooze, the blood and other fluids must be wiped away from the skin surface repeatedly so that the artist can see the skin. Such cleansing is typically accomplished using a water-based soap solution. Accordingly, a tattoo stencil generally uses a dye that is water-insoluble so that the reference outline is not washed away as the skin is cleaned. This precludes the use of many aqueous inks for tattoo reference stencils.

An inkjet printer is a type of computer printer that reproduces a digital image by propelling variably-sized droplets of liquid or molten material (ink) onto a page. Inkjet printers are the most common type of printer and range from small, inexpensive consumer models to very large and expensive professional machines. Compared to earlier consumer-oriented color printers, inkjet printers have a number of advantages. They are quieter in operation than impact dot matrix or daisywheel printers. They can print finer, smoother details through higher printhead resolution, and many consumer ink-jet printers with photographic-quality printing are widely available.

Contemporary inkjet printers use three primary ink deposition technologies: thermal, piezoelectric, and continuous. Most consumer inkjet printers produced by Lexmark, Hewlett-Packard, and Canon are thermal-type inkjet printers, which are not related to the aforementioned thermal printers that use thermal paper. Rather, thermal inkjet printers use print cartridges with a series of tiny, electrically heated chambers. To produce an image, the printer runs a pulse of electrical current through the heat chambers, causing steam to form a bubble that propels a droplet of ink onto the paper. Thermal inkjet print heads generally require water in order to perform properly. The aqueous inks used by these inkjet printers are typically based on a mixture of water, glycol and dyes or pigments. The thermal inkjet print head is generally less expensive to produce than that for other inkjet technologies. However, because thermal inkjet printers use aqueous inks, they are not generally suitable for the production of tattoo stencils whereby the aqueous ink would be transferred to the skin. Moreover, water-insoluble, solvent-based inks and dyes, without modification, are not usable in such ink jet printers because they clog the print head channels.

A dye formulation or composition suitable for use in a thermal ink jet printer is disclosed that does not cause clogging of the print head channels and is sufficiently water insoluble when attached to the skin for use in tattoo reference marking. Moreover, the disclosed dye formulations are non-toxic, hypoallergenic and suitable for use on human skin.

One component of an exemplary disclosed formulation is a dye. Dyes are colored, ionising and aromatic organic compounds that show an affinity towards the substrate (e.g., skin) to which they are applied. Normal skin pH is somewhat acidic and in the range of 4.2. to 5.6. Accordingly, particularly suitable dyes for use in the disclosed formulations include those dyes that are colored and show an affinity toward the substrate (e.g., skin) in the pH range of about 4.2. to 8.0 (the skin surface is often made temporarily more basic by cleansing with soap). These dyes stain the skin, thereby remaining thereon even when wiped with an aqueous soap solution. Suitable dyes are typically used as acid-base indicators and biological tissue stains. Dyes may also include a mordant to increase the fastness of the dye to the surface on which it is applied.

Dyes are generally available in aqueous solutions. When used in the disclosed formulations, the water in the formulation allows to dye to work in the ink-jet printer. All disclosed formulation components are by weight percent.

A particularly suitable dye type is a cationic dye, which shows an affinity for adhering to skin. An oily or greasy dye is particularly suitable because skin is also oily/greasy and so such dyes adhere favorably. Suitable dyes include, for example, methyl violet (purple), resorcin blue (blue), fuchsin (red), nigrosin (black), methyl yellow (yellow) and aniline green (green). Dyes can also be mixed to produce other colors. An exemplary composition contains from 0.001 to 25 weight percent cationic dye; preferably from 1 to 15 weight percent cationic dye; and even more preferably from 2 to 8 weight percent cationic dye.

Another component of the formulation is a solvent or solvent mixture that homogeneously suspends the dye in the formulation. Water as a solvent allows the formulation to be used in an ink jet printer. Other solvents (usually in a concentration range of 0.001 to 50 weight percent; preferably between 1 and 10 weight percent; more preferably between 3 and 7 weight percent) prevent the print head from clogging. Suitable solvents include, for example, water (preferably filtered and distilled); isopropyl alcohol; aliphatic alcohols (e.g., ethanol, methanol, n-propanol, i-propanol); ketones (e.g., acetone, 2-butanone); polyhydroxylic alcohols (e.g., propylene glycol, glycerin, 1,4-butane diol, butylene glycol); carboxylic acids (e.g., acetic acids); poly(ethylene oxide) polyethers (e.g., PEO 100 or 200 or 400 or 600); N-methylpyrrolidinone; polyethylene glycol (e.g., low molecular weight PEG 200, PEG 400); ethylene glycol dimethyl ether (e.g., glyme) and mixtures thereof. An exemplary composition contains from 75 to 99.999 weight percent solvent (including water); preferably from 85 to 99 weight percent solvent; and even more preferably from 92 to 98 weight percent solvent.

Another component of the formulation may be a humectant in a concentration range of 0.001 to 15 weight percent. A humectant prevents the composition from drying out. Examples of suitable humectants include, for example, propylene glycol, glycerin, butylene glycol, sugars (e.g., glucose, fructose, corn syrup, high fructose corn syrup), and sugar alcohols (e.g., sorbitol).

Still another component of the formulation may be a pH modifier. Such a modifier may be used to adjust the pH of the formulation to a range of about 4 to 8 to make the formulation skin-friendly and maintain the dye color. Examples of suitable pH modifiers include acids (e.g., HCl, acetic acid) and bases (e.g., NaOH, $NaHCO_3$).

Yet another component of the formulation may be a preservative in a concentration range of 0.001 to 5 weight percent. Such a preservative is used to suppress microbial (e.g., mold) growth. Examples of suitable preservatives include, for example, Germaben sold by ISP, methylparaben, benzoic acid, sodium benzoate, sorbic acid and sodium sorbate.

Another component of the formulation may be a viscosity modifying agent in a concentration range of 0.001 to 20 weight percent. Still another component of the formulation may be a fragrance in a concentration range of 0.001 to 10 weight percent.

An exemplary dye formulation of the present disclosure comprises about 7 weight percent methyl violet, about 7 weight percent isopropyl alcohol, about 14 weight percent glycerin and about 72 weight percent water. Methyl violet is a derivative of pararosaniline, used as an antiallergen and bactericide, acid-base indicator, biological stain, and textile dye.

In an exemplary method for producing a disclosed composition, one mixes the alcohol and glycerin together and then dissolves the methyl violet in the alcohol and glycerin mixture to form a first solution. One dissolves any other components in the water to form a second solution. The first and second solutions are mixed together using a vortex or standard laboratory mixer.

In an exemplary embodiment, a dye formulation is filtered to remove particulates that are greater than 25 microns is diameter to prevent print head clogging. It is preferred that the formulation not contain particles greater than 10 microns in diameter. In some cases, the formulation does not contain particulates greater than 5 microns in diameter. In still other cases, the largest particulates are 2 microns in diameter. In yet other cases, the formulation does not contain particles greater than 0.25 microns in diameter. In an exemplary method, a dye formulation is filtered through a 5-micron biological filter. The formulation is then filtered again through a 5-micron biological filter. In another method, a dye formulation is filtered through a 2-micron biological filter and then a 0.25-micron biological filter. In the filtration steps, a biological filter suitable for medical use is chosen because of its sterility; however, other filters may also be used. Because the filtering takes out particulate matter that is greater than 25 microns in size, the resulting formulations do not clog the print head of typical ink jet printers.

In an exemplary embodiment, a dye formulation is sterilized by exposure to gamma radiation or EO (Ethylene Oxide) gas. It is then injected into an ink cartridge suitable for use in an ink-jet printer. Dye formulations created in accordance with the present disclosure do not generally cause clogging of the print heads. If clogging does occur, such clogs may be dissolved by either running the print head cleaning program on the printer or removing the print head and cleaning the head with an alcohol solution. In one embodiment, a dye formulated as disclosed herein is sold in a sealed syringe cartridge so that a tattoo artist can easily fill a refillable ink cartridge with the dye. In another embodiment, the dye formulations disclosed herein are pre-filled into ink cartridges that are suitable for use in ink-jet printers.

In many cases, a customer desires a full-color tattoo. The customer may choose flash art, an artist's original artwork, or another graphic. A set of flash art often provides two versions of the art: a full-color rendering and an outline rendering for providing a reference stencil on the skin. If the artist uses his own artwork or art from another source, he subsequently makes an outline rendering for the stencil. In the current state of the art, the stencil is a single-color line drawing of the graphic. The outline rendering has traditionally been required because of the single-color stencil limitations. If a full-color graphic were copied by a thermal printer, the result would be a completely shaded, single-color graphic, which would not be helpful for feature reference purposes.

After the outline stencil is transferred to the customer's skin, the lines are used as a reference for the artist as he applies the tattoo ink while continuously checking the full-color drawing as he works to copy the details of the graphic. The formulations of this disclosure allow for the creation of a full-color stencil that transfers all the details of the original drawing to the customer's skin. Color dye cartridges compatible with an ink jet printer are provided in an exemplary embodiment to allow for the printing of multi-colored and full-color stencils. Thus, stencils printed in accordance with the disclosure offer a more detailed reference for the tattoo artist than a state-of-the-art single color outline. This allows for more accurate and efficient work by the artist. The products and methods of the disclosure also eliminate the need to create an outline rendering of a graphic, thereby saving time and effort.

Figure 2:
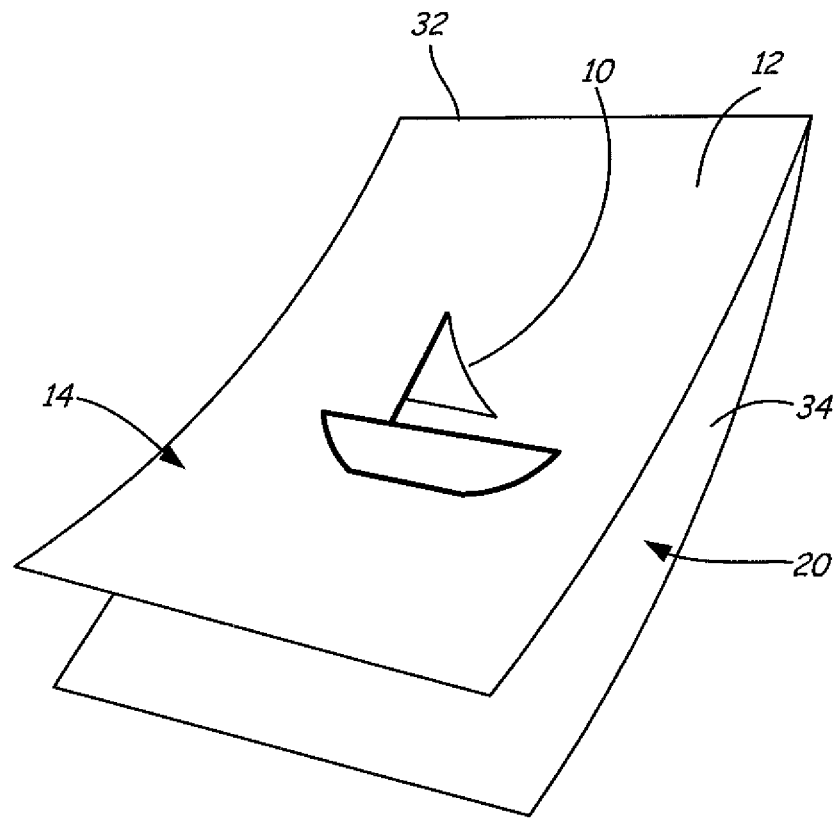
FIG. 2 is an illustration of an exemplary art kit of the present disclosure.
Figure 3:
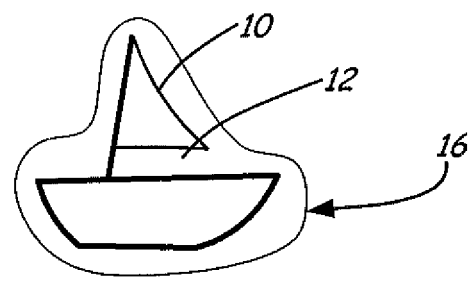
FIG. 3 is an illustration of an exemplary stencil of the present disclosure.
Figure 4:
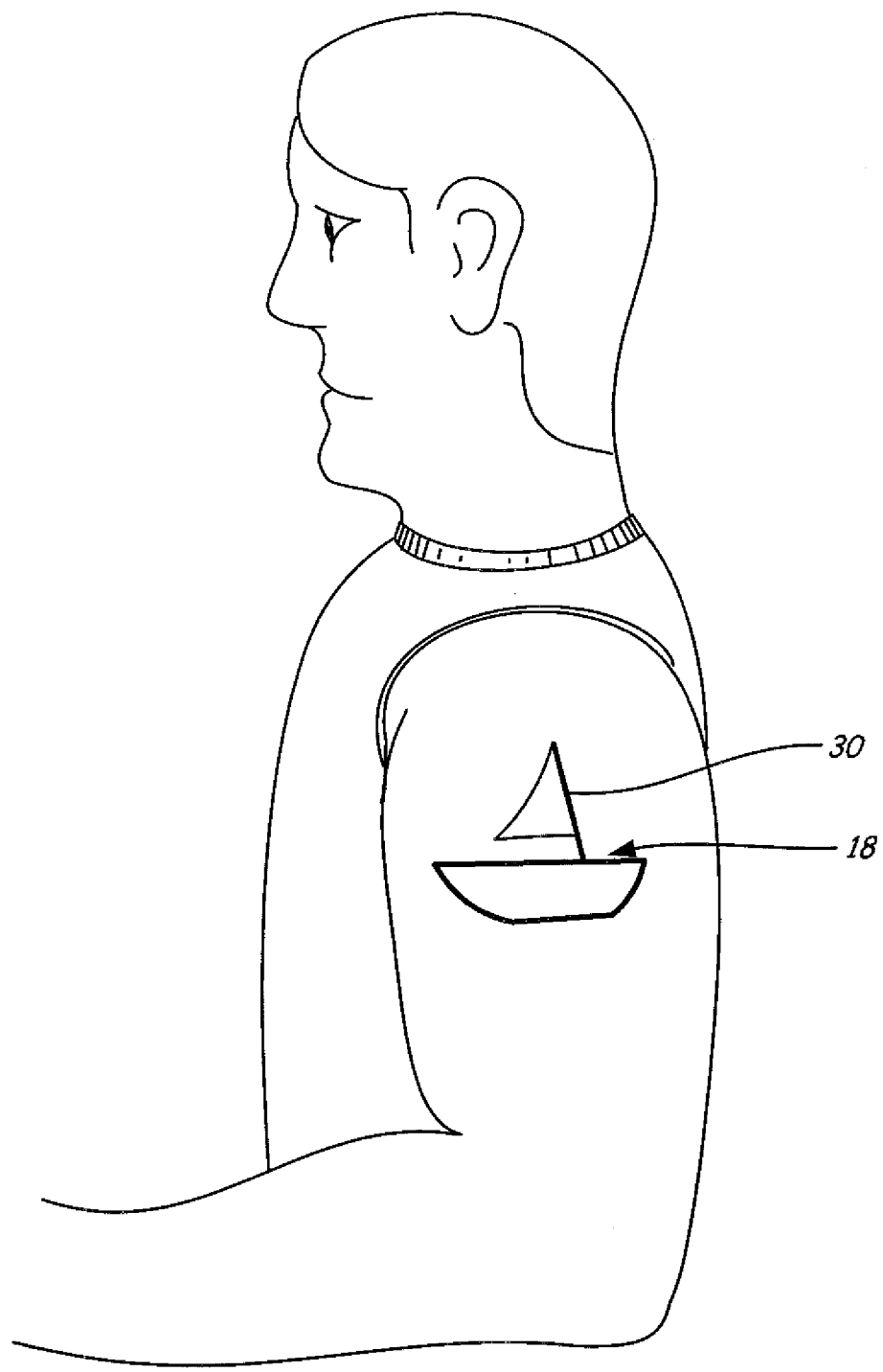
FIG. 4 is an illustration of an exemplary transferred graphic of the present disclosure.

A method of creating a stencil in accordance with the present disclosure in illustrated in FIG. 1. Such a method includes, in exemplary embodiments, obtaining a graphic to be tattooed in a computer-printable form by means including downloading the graphic from the Internet, scanning a hard copy graphic, opening an email attachment containing the graphic, and creating or manipulating a computer-drawn graphic, for example. Artists can use software to virtually wrap the tattoo around a body part to be tattooed, by either using a scanned photograph of the customer or a generic form to see how the tattoo will look in a three-dimensional format. If changes such as those to the scale or aspect ratio of the tattoo are desired, those changes can be electronically before printing the image. If the graphic is asymmetric and it is desirable for the tattoo to maintain the original orientation of the graphic, software may be utilized to obtain a mirror image of a desired graphic. As illustrated in block 22 of FIG. 1 and in FIG. 2, the mirror image 10 is then printed onto a first major surface 12 of a sheet 14 using an inkjet printer having the disclosed dye formulation(s) in the print head cartridge(s). As illustrated in FIG. 3, the sheet 14 is cut around the printed image 10 to form a stencil 16. As depicted in block 24 of FIG. 1, a user's skin surface is moistened. As illustrated in block 26 of FIG. 1 and in FIG. 4, the printed image 10 is transferred by pressing the printed side 12 of the stencil against the customer's moistened skin 18. As depicted in block 28 of FIG. 1, removing the stencil 16 from the user's moistened skin 18 leaves the transferred image 30 on the skin 18.

As disclosed herein, a printed image 10 may also be pre-printed onto a flexible substrate 14 so that it is ready to be applied to a customer's skin 18. In an embodiment, the stencil 16 may also be pre-cut around the design to further eliminate steps required of the artist. Such pre-printed stencils would be feasible because inexpensive, readily available papers can be used with the disclosed ink formulations. Moreover, the disclosed printed images 10 are stable and have a long shelf life.

A further advantage of the products and methods of the present disclosure is that they allow for printing of the printed image 10 on any suitable flexible substrate 14. This eliminates the need for expensive specialty papers such as thermal paper or hectograph paper. The disclosed formulations will print acceptably (e.g., with clarity and without running or smearing) onto many sheet materials, such as plain printer paper. However, a thin, flexible substrate (wood fiber or polymer-based) such as tracing paper, wax paper, vellum, or plastic film (made of polyurethane or polypropylene, for example) is especially suitable, as it easily conforms to the skin surface for the image transfer. A light transmissive (e.g., translucent or transparent) substrate is also desirable because it allows for visual inspection of the image on the skin for accurate placement. Further, printing onto a coated, semi-porous or non-porous transfer substrate allows for more of the dye to be transferred to the skin, resulting in a clearer reference image. Because some ink jet printers may not reliably feed such thin, flexible substrates, such a substrate 14 may be attached to a backing sheet 20 of plain printer paper for automatic feeding. Such attachment may be at an edge 32 as illustrated or by using a coating of adhesive such as a repositionable spray adhesive sold by 3M Company on first major surface 34 of backing sheet 20. The disclosure also contemplates a two-ply paper product comprising a backing sheet 20 connected to a thinner, more flexible sheet 14.

The dye formulations of the present disclosure are compatible with the transfer lotions typically used by tattoo artists to transfer the stencil from the printed substrate to the customer's skin. Moreover, unlike the ink in most standard ink jet cartridges, the dye formulations, once applied to the skin, are substantially water-insoluble and will not be washed away as the artist works. In exemplary embodiments, the dye formulations of the present disclosure are easily removed with isopropyl alcohol.

In yet another embodiment, the printed stencil image may be transferred to a user's skin and left thereon as a temporary tattoo, without further work thereon. One exemplary application is as a mock-up so that the customer can test the placement, size and coloring of the tattoo graphic on his skin for several days before committing to a permanent tattoo. Another exemplary application is for temporary tattoos for promotional branding, costuming, or children's play, for example.

Although the present invention has been described with reference to preferred embodiments, workers skilled in the art will recognize that changes may be made in form and detail without departing from the spirit and scope of the invention. In addition, any feature disclosed with respect to one embodiment may be incorporated in another embodiment, and vice-versa.

What is claimed is:

1. A method for producing a composition of matter comprising:
    producing a mixture comprising a cationic dye and a solvent;
    filtering the mixture to obtain a composition that does not have particles that are greater than 25 microns in diameter; and
    sterilizing the composition.
2. The method of claim 1 wherein the sterilizing is accomplished with gamma radiation exposure.
3. The method of claim 1 wherein the sterilizing is accomplished with ethylene oxide gas exposure.
4. The method of claim 1 wherein the composition does not have particles that are greater than 5 microns in diameter.
5. The method of claim 4 wherein the composition does not have particles that are greater than 2 microns in diameter.
6. The method of claim 5 wherein the composition does not have particles that are greater than 0.25 microns in diameter.
7. The method of claim 1 wherein the filtering is accomplished by using a plurality of filters.
8. The method of claim 7 wherein each of the plurality of filters passes particles of different sizes.
9. The method of claim 8 wherein the filtering comprises successively using filters that pass particles of decreasing size.

* * * * *